United States Patent
Trombley, III et al.

(10) Patent No.: US 7,850,659 B1
(45) Date of Patent: Dec. 14, 2010

(54) FLUID CONTAINER HOLDING DEVICE, FLUID DELIVERY SYSTEM AND METHOD OF USE THEREFOR

(75) Inventors: Frederick W. Trombley, III, Gibsonia, PA (US); Joseph J. Fularz, Lower Burrell, PA (US); Richard W. Dewit, Pittsburgh, PA (US)

(73) Assignee: Medrad, Inc., Indianola, PA (US)

( * ) Notice: Subject to any disclaimer, the term of this patent is extended or adjusted under 35 U.S.C. 154(b) by 1883 days.

(21) Appl. No.: 10/921,788

(22) Filed: Aug. 18, 2004

Related U.S. Application Data

(60) Provisional application No. 60/481,255, filed on Aug. 18, 2003.

(51) Int. Cl.
  *A61M 5/32* (2006.01)
(52) U.S. Cl. ................ 604/174; 604/178; 604/179; 248/74.1; 248/74.2
(58) Field of Classification Search ............... 604/174, 604/178–179, 181, 182, 322, 342, 345; 248/313, 248/74.1, 74.2, 74.3; 292/4–8
See application file for complete search history.

(56) References Cited

U.S. PATENT DOCUMENTS

| | | | | |
|---|---|---|---|---|
| 1,647,039 A | * | 10/1927 | Fischer | 248/309.1 |
| 2,462,442 A | * | 2/1949 | Wallace | 248/538 |
| 2,566,496 A | * | 9/1951 | Montano | 248/514 |
| 3,651,832 A | * | 3/1972 | Meyer | 137/615 |
| 4,187,845 A | * | 2/1980 | Dror | 128/205.13 |
| 4,486,044 A | * | 12/1984 | Gordon et al. | 294/31.2 |
| 4,623,343 A | | 11/1986 | Thompson | |
| D289,435 S | | 4/1987 | Fischione | |
| 4,690,674 A | | 9/1987 | Dalglish | |
| D293,469 S | | 12/1987 | Greenblatt | |
| D295,315 S | | 4/1988 | Nelson | |
| D297,053 S | | 8/1988 | Janzen | |
| 4,838,857 A | * | 6/1989 | Strowe et al. | 604/67 |
| 4,893,849 A | * | 1/1990 | Schlack | 292/7 |
| 4,952,205 A | | 8/1990 | Mauerer | |
| 4,976,696 A | | 12/1990 | Sanderson | |
| 5,135,125 A | | 8/1992 | Andel | |
| 5,244,461 A | | 9/1993 | Derlien | |
| 5,271,649 A | * | 12/1993 | Gromotka | 292/113 |
| 5,383,858 A | | 1/1995 | Reilly | |
| D365,633 S | | 12/1995 | Walker | |
| 5,490,658 A | | 2/1996 | Coward | |
| D373,823 S | | 9/1996 | Baldwin | |
| 5,749,490 A | | 5/1998 | Keicher | |

(Continued)

OTHER PUBLICATIONS

Baxter Healthcare Corp., Brochure No. 7-36-30-593, Aug. 2002.

*Primary Examiner*—Nicholas D Lucchesi
*Assistant Examiner*—Quynh-Nhu H Vu
(74) *Attorney, Agent, or Firm*—James R. Stevenson

(57) ABSTRACT

An apparatus for holding a fluid container, such as a syringe or a vial, is provided for securing the container in an upside down or other suitable position for use in various medical procedures such as those of the type that involve use of a medical pump. The fluid container holding apparatus is capable of operatively connecting to any of a number of support structures including a wall, ceiling, desk, table, post, hangar, or IV stand. A fluid delivery system including such a fluid container, and a fluid conduit, such as IV tubing, may include the fluid container holding apparatus of the present invention.

11 Claims, 13 Drawing Sheets

U.S. PATENT DOCUMENTS

| | | | | |
|---|---|---|---|---|
| 5,830,194 A * | 11/1998 | Anwar et al. | | 604/223 |
| D411,882 S | 7/1999 | Minasian | | |
| 6,036,858 A * | 3/2000 | Carlsson et al. | | 210/232 |
| D424,692 S | 5/2000 | Monaghan | | |
| 6,135,409 A * | 10/2000 | O'Keeffe | | 248/314 |
| 6,261,254 B1 * | 7/2001 | Baron et al. | | 604/323 |
| D456,603 S | 5/2002 | Phetthaweebancha | | |
| 6,565,054 B2 | 5/2003 | Weesner | | |
| 6,607,512 B2 * | 8/2003 | Oliver et al. | | 604/209 |
| 6,682,506 B1 * | 1/2004 | Navarro | | 604/174 |
| 6,699,258 B1 * | 3/2004 | Sadler et al. | | 606/157 |
| 6,769,659 B1 * | 8/2004 | Martello | | 248/311.2 |
| 7,662,124 B2 * | 2/2010 | Duchon et al. | | 604/19 |
| 7,722,584 B2 * | 5/2010 | Tanaka et al. | | 604/317 |
| 2002/0074476 A1 * | 6/2002 | Cooner et al. | | 248/551 |
| 2002/0107481 A1 | 8/2002 | Reilly | | |
| 2002/0177821 A1 | 11/2002 | Barak | | |

* cited by examiner

FLUID CONTAINER HOLDING DEVICE, FLUID DELIVERY SYSTEM AND METHOD OF USE THEREFOR

CROSS-REFERENCE TO RELATED APPLICATION

This application for patent claims the benefit of U.S. Provisional Application Ser. No. 60/481,255 titled Fluid Container Holding Device, Fluid Delivery System, And Method Of Use Therefor, filed 18 Aug. 2003. This provisional application has been assigned to the assignee of the invention disclosed below, and its teachings are incorporated into this document by reference.

FIELD OF THE INVENTION

The invention relates generally to systems and methods, and associated devices, for holding fluid containers. More particularly, the invention relates to fluid container holding devices for fluid delivery systems, and a fluid delivery system incorporating such a fluid container holding device. The invention also pertains to methods of use for the fluid container holding device and the fluid delivery system.

BRIEF DESCRIPTION OF RELATED ART

The following information is provided to assist the reader to understand the invention disclosed below and the environment in which it will typically be used.

Countless medical procedures are conducted throughout the world on a daily basis. A myriad of different fluids may be administered to a patient to serve a variety of different purposes: feeding fluids to nourish parenterally, saline to hydrate, analgesics to suppress pain, therapeutic drugs to treat disease, contrast media to enhance images of organs and other internal bodily structures, etc. Many of these medical procedures require the use of a medical pump similar to that disclosed in U.S. Patent Application Publication 2002/20177821, filed on Jan. 25, 2002, the disclosure of which is incorporated herein by reference. Medical pumps of this type generally administer fluid from three primary types of containers: bottles, syringes, and bags.

Each of the three primary types of fluid containers has its own traditional methods and apparatuses for securing the respective fluid container properly in medical procedures. Bags, which are the most common form of fluid container, generally have a hole punched into the top of the bag so that the bag may hang from a hangar. Hangars to support fluid bags in medical procedures can be placed in a myriad of different places relative to the medical pump. As long as the intraveneous (IV) tubing is long enough to travel from the discharge end of the bag to the medical pump and then to the patient, there seems to be no limit as to where hangars may be placed. Basically any rigid structure is strong enough to support a fluid bag hangar, and to that end hangars can be placed on the IV stand, ceilings, walls, and other structures. The most common placement for a bag hangar is clearly on the IV stand, and such a hangar is disclosed in U.S. Pat. No. 4,690,674, the disclosure of which is incorporated herein by reference.

Bottles, the second most common type of fluid container in medical procedures, present more of a problem. Bottles can vary radically in size and shape, and as a result many different apparatuses have been developed to secure bottles for medical procedures. There exist several different types of clips, hangars, and mounting structures for supporting bottles for medical procedures. For example, U.S. Pat. No. 5,749,490, the disclosure of which is incorporated herein by reference, discloses a bottle holder that may be hung on a hook on a wall. U.S. Pat. No. 5,135,125, the disclosure of which is incorporated herein by reference, discloses a bottle hangar made of film that is intended to hang from a hook on an IV stand. U.S. Pat. No. 5,490,658, the disclosure of which is incorporated herein by reference, discloses a hangar apparatus comprising two hanging strips to support a bottle, and is capable of hanging from a hook on an IV stand. U.S. Pat. No. D456,603, the disclosure of which is incorporated herein by reference, discloses an ornamental design for a bottle holder with a clip for securing the apparatus. Finally, there exists the crude method of simply securing a bottle to a wall, IV stand, or other support structure with tape, glue, or some other adhesive.

Holders for syringes, such as those disclosed in U.S. Pat. No. 5,383,858, the disclosure of which is incorporated herein by reference, have been the subject of the least development. Traditionally, it has been difficult to draw fluid from the discharge end of a syringe in the same fashion that fluid is drawn from bags and bottles. Previously, to use a syringe in a medical procedure required the use of a Harvard medical pump, a type of pump that directly interacts with the syringe plunger to expel fluid from the syringe. Harvard medical pumps generally have syringe holders that are integral to the design of the pump. Harvard medical pumps exist in contrast to the type of medical pump disclosed in U.S. Patent Application Publication 2002/20177821, filed on Jan. 25, 2002, the disclosure of which is incorporated herein by reference, which draws fluid from the discharge end of a fluid container. Because bottles, bags, and other fluid containers had to be used in conjunction with a type of medical pump different from that used in conjunction with syringes, the traditional methods of securing a fluid container were acceptable.

U.S. Patent Application Publication 2002/0107481, filed on Feb. 4, 2002, by the same Assignee as the subject application, the disclosure of which is incorporated herein by reference, provides a syringe loading device which overcomes some of the aforementioned hurdles in designing such a device. Therein, a holding assembly, which may comprise at least one fixed support connected at a mounting plate and at least one movable support connected to the mounting plate, is provided. In addition, the movable support is movable between an engaged position contacting the body of at least one fluid container for maintaining the at least one fluid container in the holding assembly and a disengaged position out of contact with the body of the fluid container. The present invention disclosed herein provides fluid delivery systems, as well as fluid container holding devices and methods, that constitute an improvement over those disclosed in U.S. Patent Application Publication 2002/0107481.

These improved systems, devices, and methods of securing a fluid container for a medical procedure have been facilitated by new systems, devices, methods, and other devices such as the syringe spike described in U.S. Pat. No. 4,623,343 and cited on Brochure No. 7-36-30-593 published in August 2002 by Baxter Healthcare Corporation, the disclosures of which are incorporated herein by reference. These connectors and spikes have been developed to enable syringes to be used on virtually any medical pump, not just Harvard-type medical pumps. These new developments were not immediately met by the advent of new systems, apparatuses, and methods that are capable of securing several different types of fluid containers in medical procedures.

From the foregoing, it is clear that the current technology for securing fluid containers not only imposes undue costs but also causes delay and other inefficiencies in countless medical procedures in hospitals, clinics and other medical institutions.

For the foregoing reasons, there is a need for new apparatuses, systems, and methods, for securing a fluid container in medical procedures.

SUMMARY OF THE INVENTION

Several objectives and advantages of the invention are attained by the various embodiments and related aspects of the invention summarized below.

In a presently preferred embodiment, the invention provides an apparatus for holding a fluid container. The apparatus includes a primary base, a platform, and a closure. The primary base defines a region adapted to engage at least a portion of the fluid container. The platform is operatively connected to the primary base and is adapted to engage at least a portion of the fluid container. The closure is operatively connected to the primary base for holding at least a portion of the fluid container against the primary base. In a preferred implementation, the closure includes first and second support arms and a gate. The first support arm is adjustably connected to the primary base, and the second support arm is also connected to the primary base. The gate is operatively connected to the first support arm and is therein enabled to be moved between (i) a closed position in which the gate interlinks the first and second support arms to enable the fluid container to be securely held against the primary base and (ii) an open position in which access and egress to the primary base is provided to the fluid container. In another implementation, the closure may include a strap, tape, or a secondary base adjustably interconnected with the primary base via at least one support arm.

In another related embodiment, the invention provides a fluid delivery system. The system includes a fluid container, a fluid conduit, a medical infusion device, and a container holding apparatus. The fluid conduit is connected to the fluid container for receiving fluid therefrom. The medical infusion device is adapted to interact with the fluid conduit for controlling flow of the fluid therethrough and ultimately into a patient. The container holding apparatus includes a base and a closure. The base defines a region adapted to engage at least a portion of the fluid container, and the closure is operatively connected to the base for holding at least a portion of the fluid container against the base. In a preferred implementation, the closure includes first and second support arms and a gate. The first support arm is adjustably connected to the base, and the second support arm is also connected to the base. The gate is operatively connected to the first support arm and is therein enabled to be moved between (i) a closed position wherein the gate interlinks the first and second support arms to enable the fluid container to be securely held against the base and (ii) an open position wherein access and egress to the base is provided to the fluid container. In another implementation, the closure may include a strap, tape, or a secondary base adjustably interconnected with the base via at least one support arm.

BRIEF DESCRIPTION OF THE DRAWINGS

The invention and its various embodiments will be better understood by reference to the detailed disclosure below and to the accompanying drawings, wherein.

Figure 1:
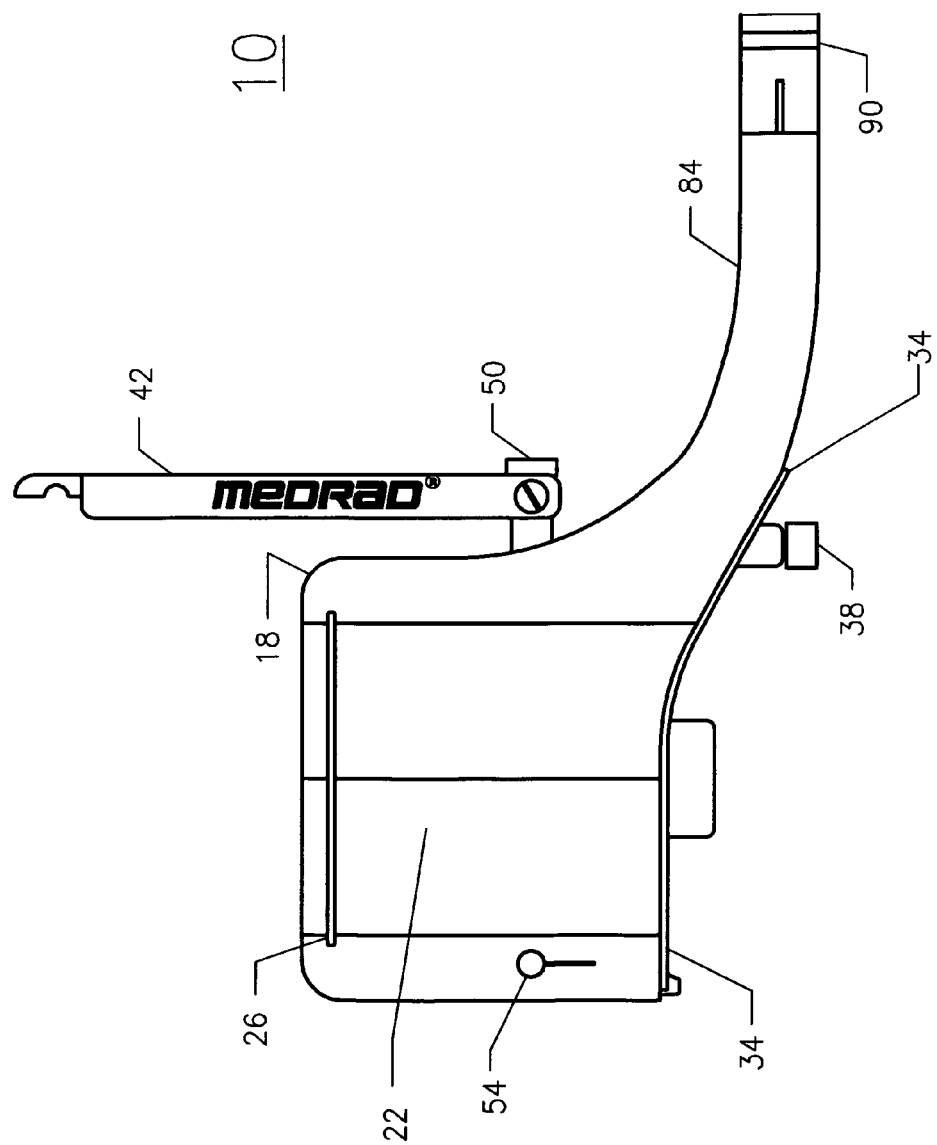
FIG. 1 illustrates a front perspective view of a fluid container holding device according to a preferred embodiment of the invention.

DETAILED DESCRIPTION OF THE PRESENTLY PREFERRED AND ALTERNATIVE EMBODIMENTS OF THE INVENTION

Although the invention herein described and illustrated is presented primarily in the context of medical uses, the reader will understand that the invention can also be applied or adapted to other types of uses in which fluids are to be dispensed. Various embodiments and related aspects of the invention will now be described with reference to the accompanying drawings, in which like elements have been designated where possible by the same reference numerals.

As used herein, the term "fluid container" refers broadly to a receptacle such as a carton, a jar, a can, a syringe, a bag, a bottle or other enclosure in which fluid is held or carried. As used herein, the term "fluid conduit" refers broadly to a pipe, a canal, a tube, a channel or other passage for conveying fluid. As used herein, the term "medical pump" refers broadly to infusion devices, such as an infusion pump, a syringe pump, or other device used in administering or infusing fluid to patients.

Figure 6:
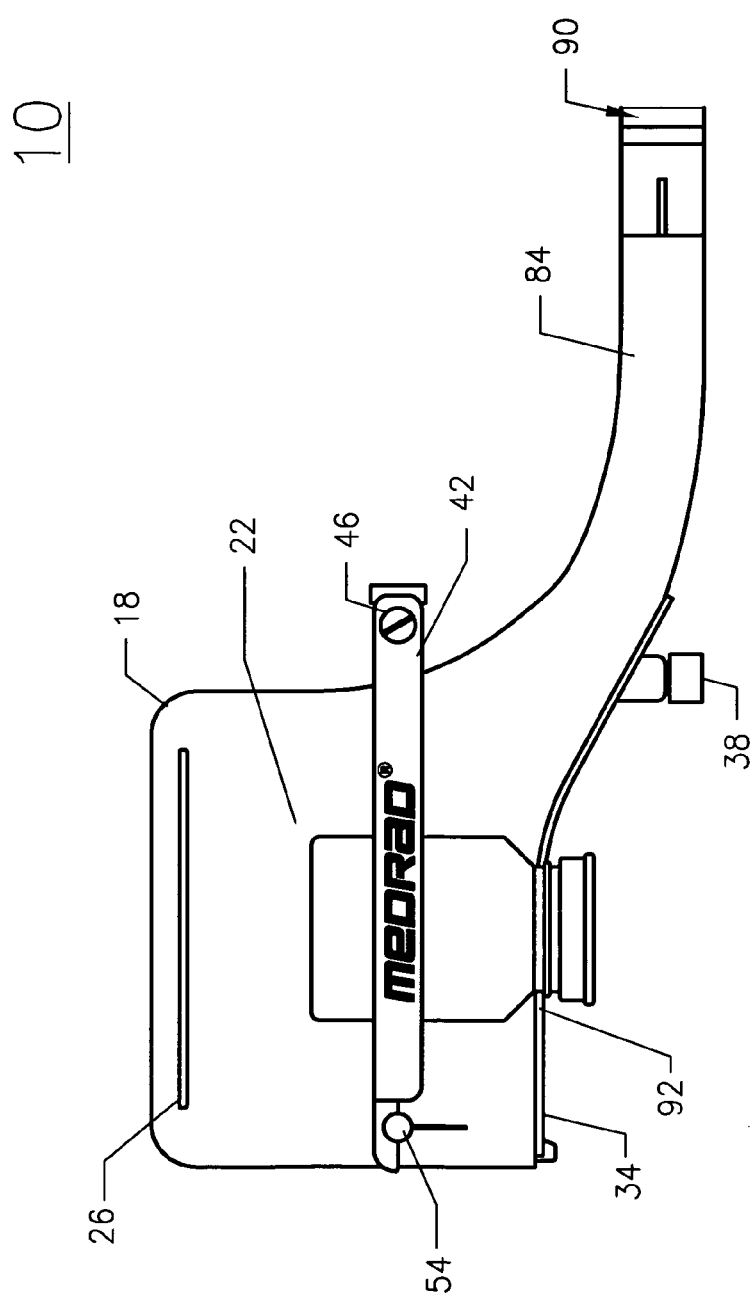
FIG. 6 illustrates a front perspective view of the fluid container holding device shown in FIG. 1 in which a bottle has been secured.
Figure 7:
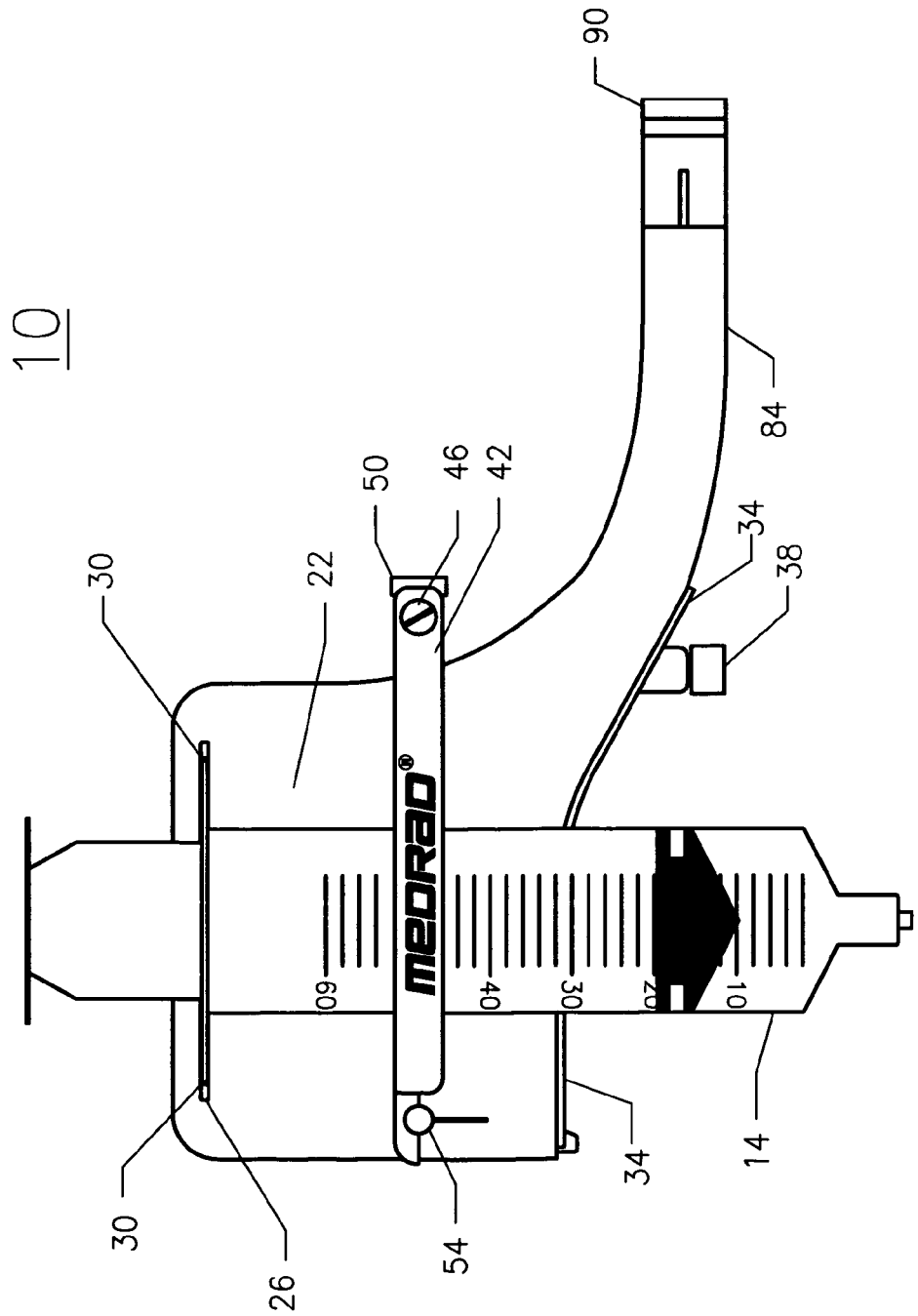
FIG. 7 illustrates a front perspective view of the fluid container holding device shown in FIG. 1 in which a syringe has been secured.
Figure 8:
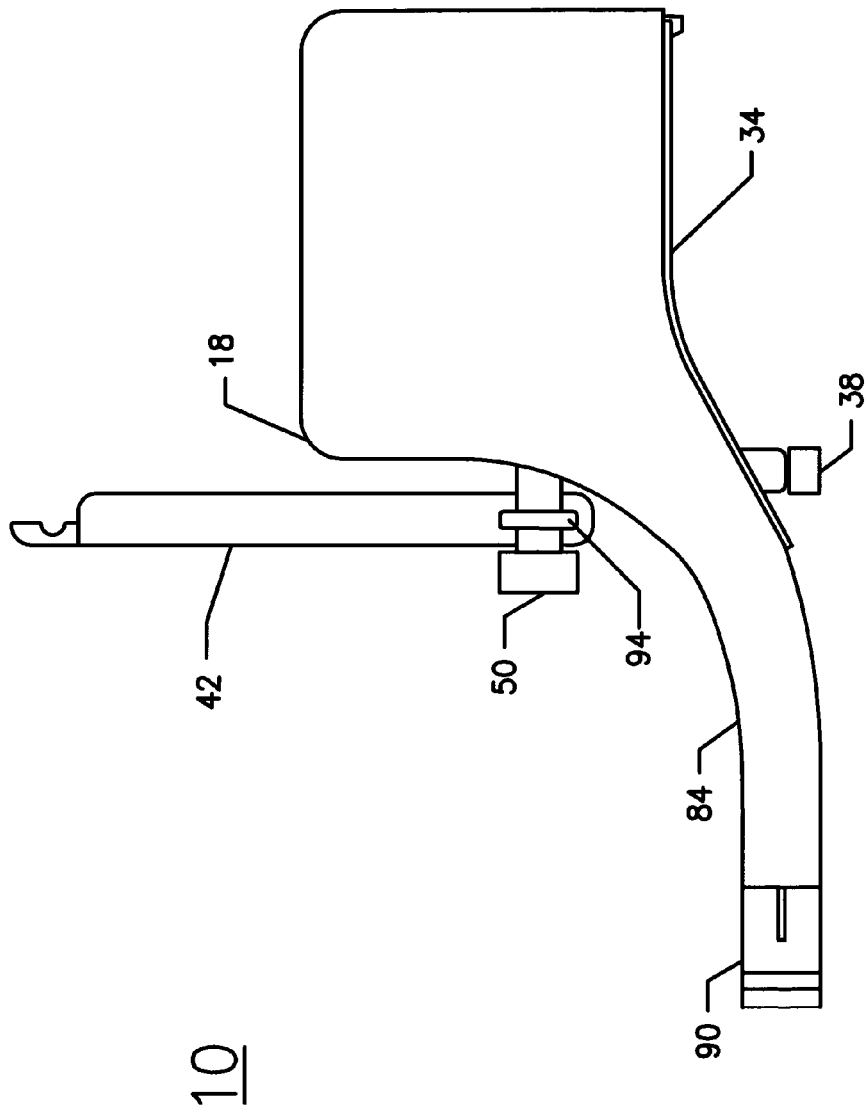
FIG. 8 illustrates a rear view of the fluid container holding device of FIG. 1.
Figure 9:
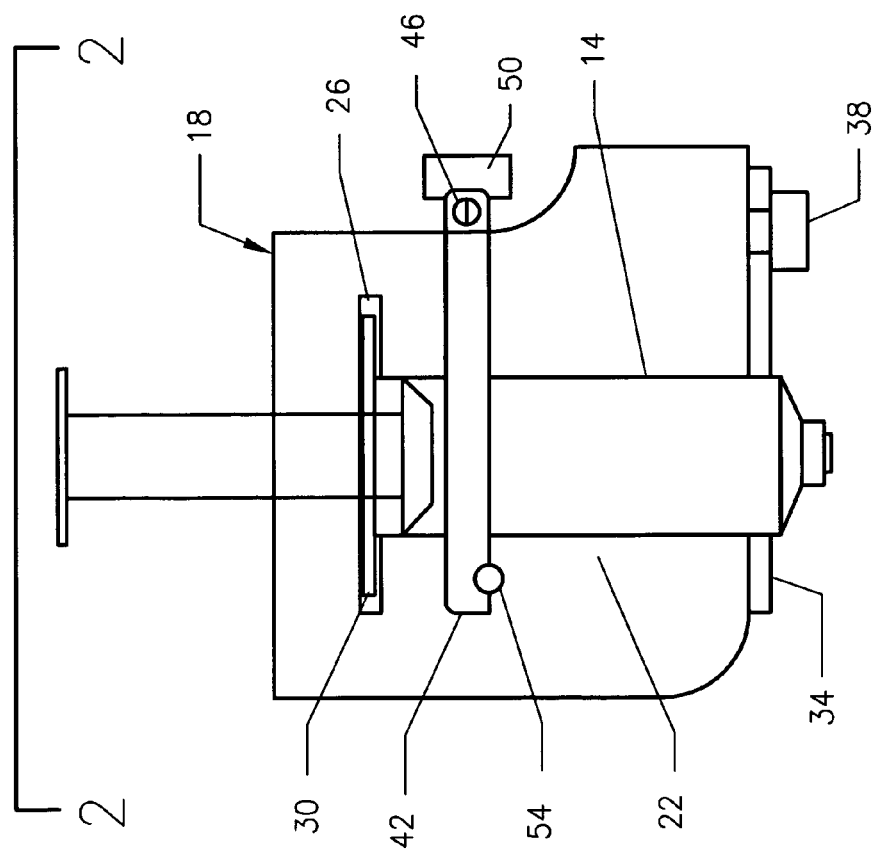
FIG. 9 illustrates a front plan schematic view of the fluid container holding device of FIG. 1 in which a syringe has been secured.

Referring now to the drawings, FIGS. 1-10 illustrate a fluid container holding device according to a presently preferred embodiment of the invention. FIGS. 1-5, 8 and 10 show the fluid container holding device, generally designated 10, empty. FIG. 6 shows the fluid container holding device 10 holding a bottle or vial 204, whereas FIGS. 7 and 9 show a syringe 14 retained by the fluid container holding device 10.

As best shown in FIGS. 7 and 9, the syringe 14 is being held in an upside-down position by the fluid container holding device 10. Fluid containers such as syringes and vials are generally secured in an inverted position during infusion procedures to promote easy flow of fluid from the discharge end of the fluid container. It requires significantly less force to draw fluid from an inverted fluid container than it does to draw fluid from an upright fluid container. If the fluid container is inverted, gravity acts to promote the flow of fluid from the fluid container; whereas if the fluid container is upright, gravity acts to restrict the flow of fluid from the fluid container.

To secure the syringe 14 against primary base 18 in an inverted position, the primary base 18 defines a substantially concave region 22 adapted to hold or engage at least a portion of a fluid container. This region, for example, could be made substantially concave so that the barrel of a fluid container, such as a syringe, can rest readily against it. One skilled in the art will recognize a multitude of ways that a primary base 18 can define a region 22 adapted to engage or hold at least a portion of the fluid container. For example, instead of defining a concave region 22, as in the embodiment of FIGS. 1-10, the primary base 18 can define a region that is at least partially convex. In such an embodiment, the fluid container holding device will be able to readily accommodate in this convexly shaped region the fluid container or portion thereof having the appropriate corresponding contour.

The region 22 that is adapted to engage or hold at least a portion of the fluid container also defines a substantially horizontal groove 26 disposed towards the top of the primary base 18. As best shown in FIGS. 7 and 9, the groove 26 is adapted to engage or hold at least a portion of the flanges 30 of syringe 14 as the barrel of syringe 14 rests against the region 22 adapted to engage or hold at least a portion of the fluid container.

Figure 2:
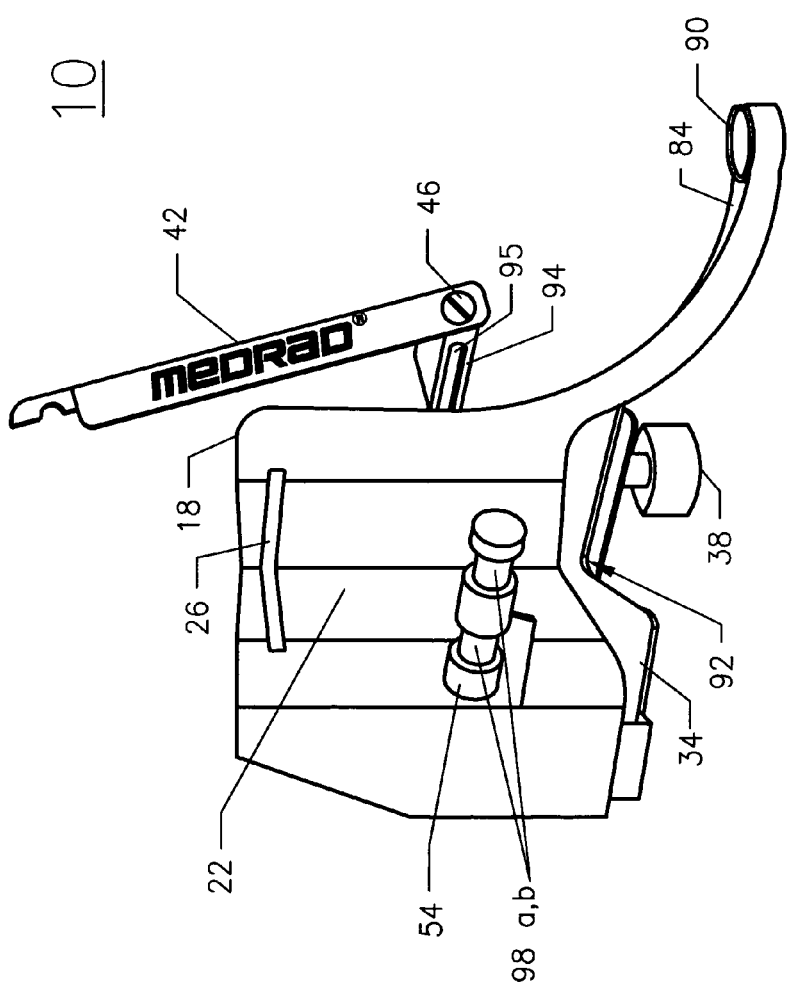
FIG. 2 illustrates a left side perspective view of the fluid container holding device shown in FIG. 1.
Figure 3:
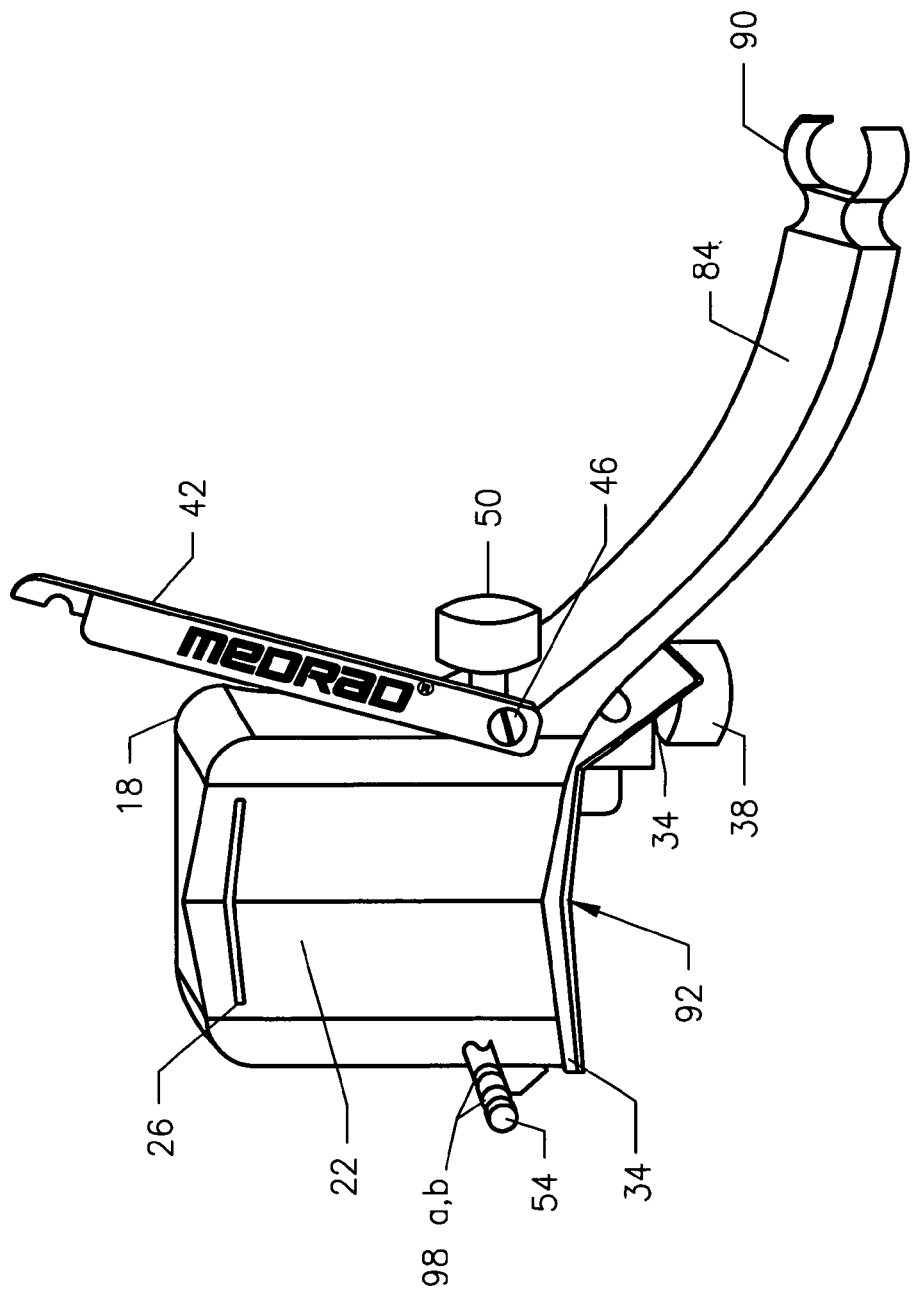
FIG. 3 illustrates a right side perspective view of the fluid container holding device shown in FIG. 1.
Figure 4:
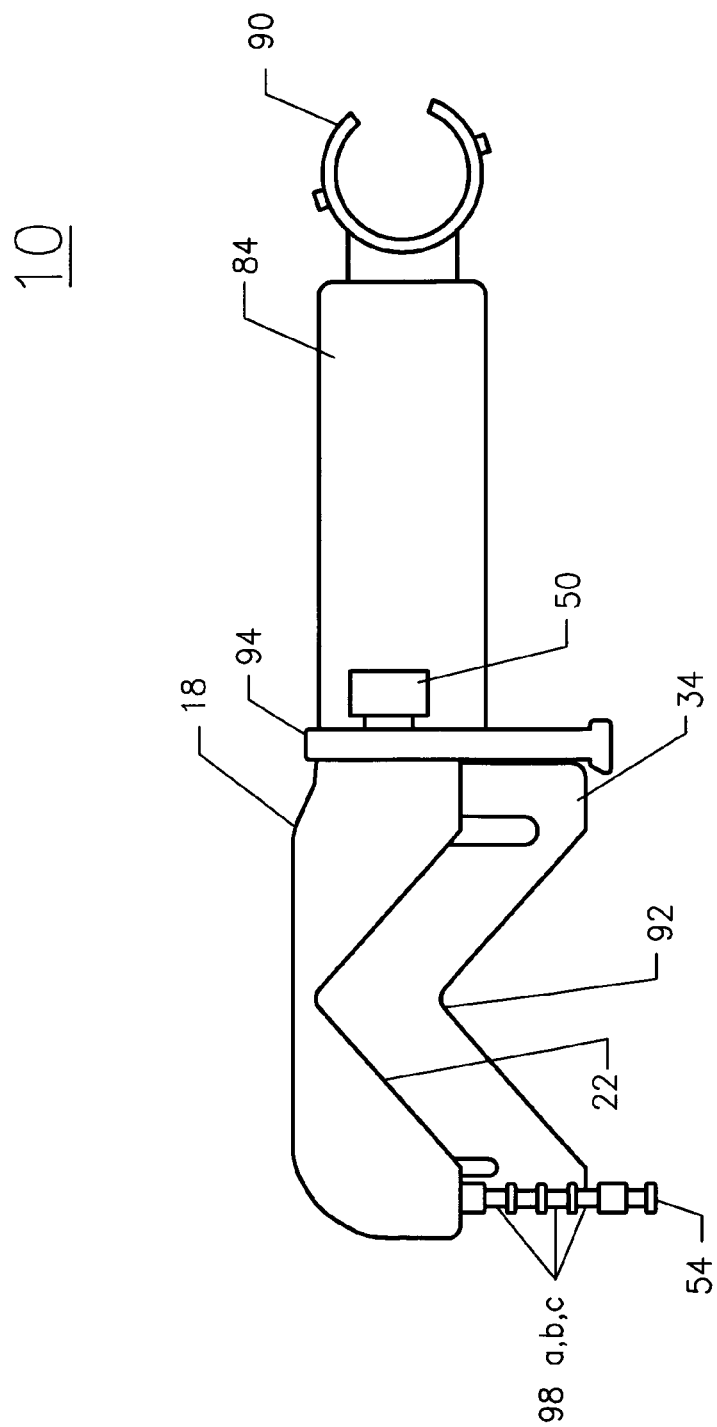
FIG. 4 illustrates a top perspective view of the fluid container holding device shown in FIG. 1.
Figure 5:
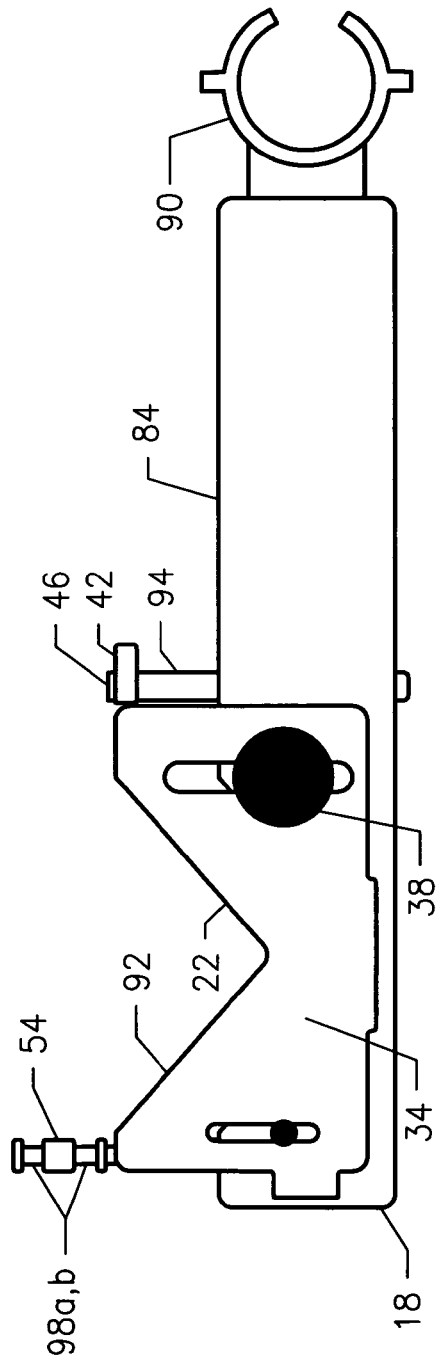
FIG. 5 illustrates a bottom perspective view of the fluid container holding device shown in FIG. 1.

The syringe 14 is further secured at least temporarily in the stationary position by a forwardly extending platform 34. The platform 34 defines a region 92, which is best shown in FIGS. 2-4, that is adapted to engage or hold at least a portion of the fluid container. The syringe 14 can at least partially rest upon the platform 34 once the platform 34 is forwardly extended from the bottom of the primary base 18; with the platform 34 at least partially encircling at least a portion of the neck of the syringe 14 to engage or hold the syringe 14 in a stationary position. A screw lock 38 is capable of locking the platform 34 into the desired position.

One skilled in the art will recognize that there are many different ways the platform 34 could operate. In embodiment of FIGS. 1-10, the platform 34 can be forwardly extended from the bottom of the primary base 18, and is capable of being locked into place through use of the screw lock 38. One skilled in the art will recognize that while this is depicted as a manual operation, it could easily be adapted to become an operation that is completed through the use of electronics, specifically a drive mechanism. Furthermore, one skilled in the art will recognize that the screw lock 38 is a very general locking mechanism, and that many effective alternatives exist, such as locking clips. In addition, while the platform 34 is said to forwardly extend from the bottom of the primary base, it should be understood that the platform 34 could just as easily rotate outwardly from beneath the primary base 18; the platform 34 in this case being rotatable around an axis disposed on the bottom portion or beneath the primary base 18.

The syringe 14 is also held in position by a gate 42, which is adapted to secure at least a portion of the syringe 14 against the primary base 18 and in the region 22 adapted to engage or hold at least a portion of the fluid container. The gate 42 is capable of being forwardly extended because it is connected to a first support arm 94 by a hinge 46, which is best shown in FIGS. 2 and 4-8. A channel 95, which is shown in FIG. 2, is cut into the middle of the first support arm 94 so that the first support arm 94 is capable of sliding about the second screw lock 50. The second screw lock 50 is designed to releasably secure the first support arm 94 and therethrough the gate 42.

The gate 42 connects to the first support arm 94 at the hinge 46, which allows the gate 42 to rotate vertically from an open position to a closed position and vice versa. In the closed position, the gate 42 interacts with notches 98a,b in the second support arm 54. This is best shown in FIGS. 2, 4, 5 and 10.

One skilled in the art will recognize many ways to fashion a closure that will hold a fluid container against a base. In embodiment of FIGS. 1-10, a syringe or a bottle is held against base 18 by a gate 42 via support arms 54 and 94, but there are other examples of effective closures: a belt, a strap, a rope, tape, or even a secondary base.

The fluid container holding device 10 is adapted to be hung on a wall by virtue of a hanger (not shown) on the back of the primary base 18. One skilled in the art will recognize many ways in which the primary base 18 could be secured for an infusion procedure. For example, the primary base 18 could easily be connected to a single support arm or a system of support arms that allow the user to operatively mount the fluid container holding device 10 on virtually any support structure. The fluid container holding device 10 could be operatively mounted on a support structure by a strap, a hanger, an adhesive, a nail, a screw, tape or any one or more of various other methods.

Furthermore, the plurality of ways in which the fluid container holding device 10 could be mounted on a support structure suggests that there are also a multitude of support structures on which the fluid container holding device could be mounted. FIGS. 1-8 and 10 illustrate an embodiment that enables a fluid container holding device to be removably mounted on an IV stand. One skilled in the art will recognize that in other embodiments of the fluid container holding device disclosed herein the aforementioned device could be permanently or removably mounted to any number of support structures including, but not limited to, an IV stand, a desk, a table, a bed frame, a wall, a ceiling, a floor, a chair, a door, or any other support structure.

Figure 10:
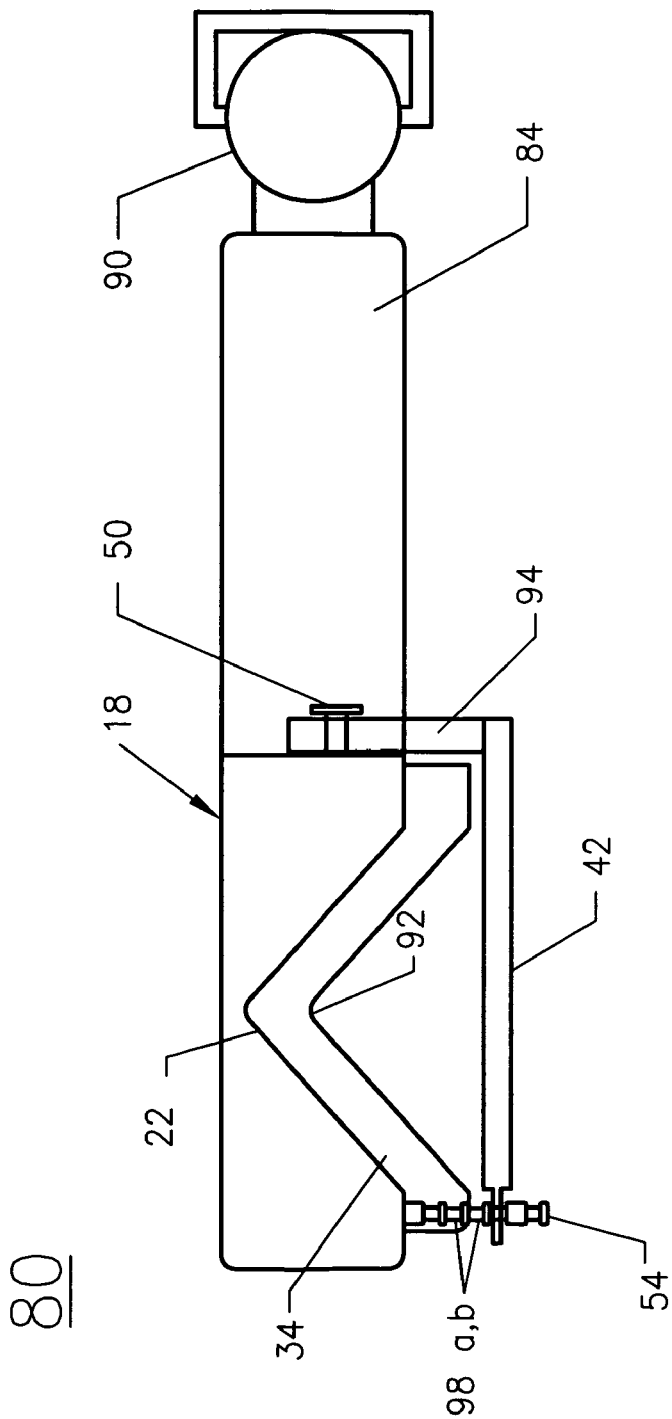
FIG. 10 illustrates a top plan schematic view taken along line 2-2 of FIG. 9 (with the syringe removed for clarity).

FIG. 10 illustrates a top plan view taken along line 2-2 of FIG. 9, with the syringe removed for clarity. Here, the primary base 18 of FIG. 10 is shown connected to a mounting arm 84. As also shown in FIGS. 1-8, the mounting arm 84 is generally long enough to ensure that the loading, unloading, and use of the fluid container in conjunction with the primary base 18 is not interfered with by other objects, such as a medical pump, which may be disposed on the IV stand. The mounting arm 84 is connected to or fashioned as a part of the primary base 18, and is adapted to removably connect to an IV stand, a bed frame, a desk, a wall, a floor, a ceiling or other external structure by a clamp 90 or other suitable mechanism. One skilled in the art will recognize that the mounting arm 84 could easily be adapted to be extendable.

One skilled in the art will recognize that while the primary base 18 is secured in a substantially upright position in this embodiment, the primary base 18 could easily be adapted to tilt, rotate or operatively tilt or rotate. For example, if the mounting arm 84 were to connect to the back of primary base 18 rather than its side, a hinge could easily be fashioned that would allow the primary base 18 to tilt vertically and allow the fluid container to be secured at different angles relative to the ground. A hinge that allows the primary base 18 to rotate horizontally could also be placed at the point where the mounting arm 84 connects to the primary base 18. A joint that allows the primary base 18 to both tilt vertically and rotate horizontally could also be utilized to increase the functionality of the fluid container holding device 10.

Furthermore, one skilled in the art will recognize that a hinge or joint need not be directly connected to the primary base 18 to facilitate the aforementioned vertical tilting or horizontal rotating. Rather, a hinged or jointed mounting arm, or system of multiple mounting arms connected by at least one hinge or joint, could also allow the primary base 18 to tilt vertically or rotate horizontally.

The primary base 18, as illustrated in FIG. 10, is the same base as shown in FIG. 9, and defines a substantially concave region 22 adapted to hold a fluid container. Any number of fluid containers, including a carton, a jar, a can, a syringe, a bag, a bottle, or other container in which fluid is held or carried can be supported by the primary base 18. The platform 34 is operatively connected to the bottom of the primary base 18 and is adapted to forwardly extend from its bottom. The platform 34 is shown in a partially extended position. In a fully retracted position, the platform 34 would be disposed completely under the base. In use, the platform 34 can be extended so that its substantially curved region 92 fits at least partially around the neck of at least a portion of the fluid container. The platform 34 can also be locked into the desired position by the screw lock 38, as discussed above in connection with FIGS. 2-4.

The fluid container holding device 10 also supports the fluid container with the gate 42. The gate 42 is capable of being forwardly extended through its interaction with the first support arm 94 via hinge 46. The channel 95 is cut into the middle of the first support arm 94 so that the arm can be slid about second screw lock 50, which is designed to releasably secure the first support arm 94, and thus gate 42, into the extended position.

The linkage of gate 42 with first support arm 94 via hinge 46 allows the gate to rotate vertically from an open position to a closed position and vice versa. In the closed position, the distal end of gate 42 interacts with notches 98*a,b* in second support arm 54.

Figure 11:
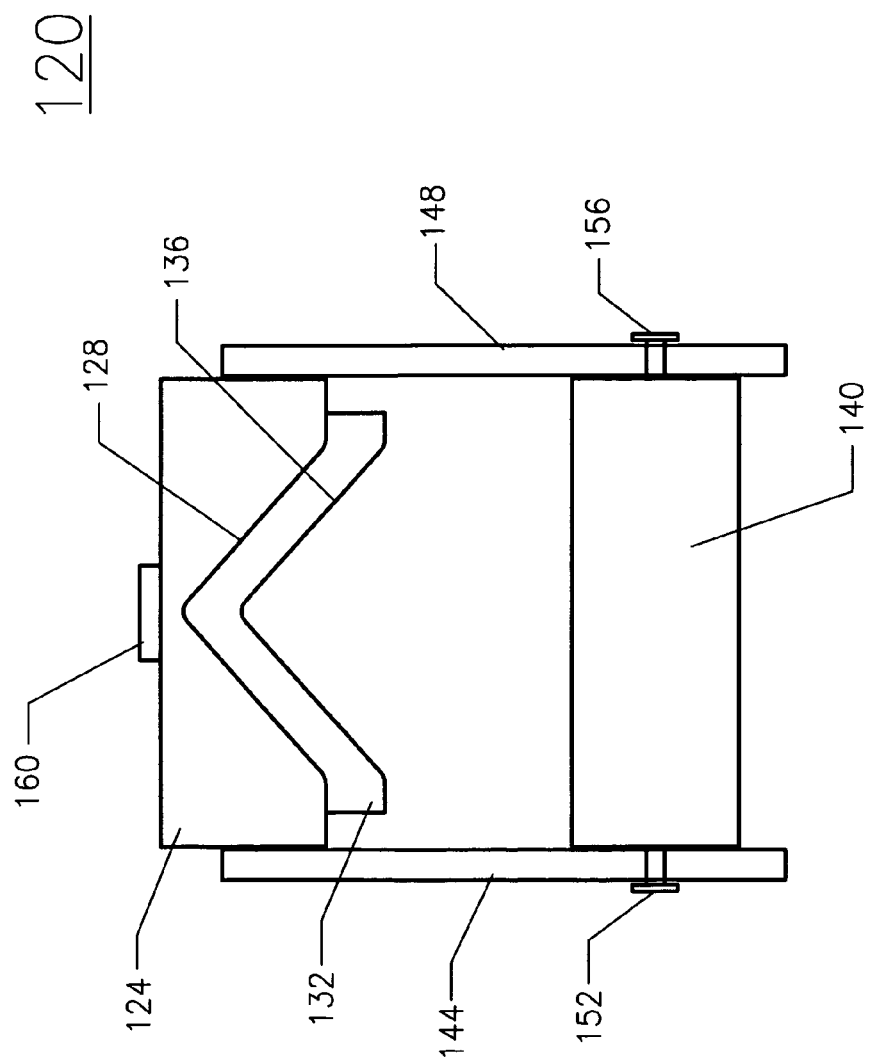
FIG. 11 illustrates a top plan schematic view of another embodiment of the fluid container holding device of the invention.

FIG. 11 illustrates a top plan view of another embodiment of the fluid container holding device 120 of the invention. In this embodiment, the fluid container holding device 120 comprises a first base 124 that defines a substantially concave region 128 adapted to engage or hold at least a portion of a fluid container. A platform 132 is operatively connected to the bottom of the first base 124, and is adapted to be forwardly extended from the bottom of first base 124. The platform 132 defines a substantially curved region 136 that is adapted to fit around at least a portion of the neck of the fluid container when at least a portion of the fluid container rests against first base 124.

The fluid container holding device 120 also includes a second base 140 that is approximately the same length and width as first base 124, though the second base 140 need not necessarily define any region that is adapted to engage or hold at least a portion of the fluid container. All sides of the second base 140 are substantially planar.

The second base 140 is operatively connected to the first base 124 by the first support arm 144 and the second support arm 148. The first support arm 144 and the second support arm 148 are connected to the sides of the first base 124. Both the first support arm 144 and the second support arm 148 define a channel (not shown) that is disposed horizontally over the respective support arm so that the first support arm 144 and second support arm 148 may slide around first screw lock 152 and second screw lock 156, respectively. This enables the second base 140 to be operatively forwardly extended relative to the first base 124, and the screw locks 152 and 156 can then be used to effectively lock the second base 140 into an extended position.

One skilled in the art will recognize that the second base 140 could easily define a region adapted to more securely engage or hold at least a portion of the fluid container against the first base 124.

The fluid container holding device 120 thus enables a fluid container to be securely held therein via the first and second bases 124 and 140. Specifically, with the second base 140 extended away from the first base 124 via support arms 144 and 148, a fluid container can be placed within the device 120. Once the fluid container is inserted, the second base 140 can then be retracted so that the fluid container is engaged by the second base 140 against the first base 124. In this manner, at least a portion of the fluid container would be in contact with both the first and second bases 124 and 140. The fluid container can be prevented from slipping from between the first and second bases by platform 132, which could be extended so that the curved region 136 of the platform 132 fits around at least a portion of the neck of the fluid container. The screw locks 152 and 156 can then be used to lock the second base 140 into the retracted position.

The fluid container holding device 120 can be secured against a wall by the hanger 160 disposed on the back of the first base 124. The hanger 160 is adapted to be removably mounted on a standard wall fitting.

Figure 12:
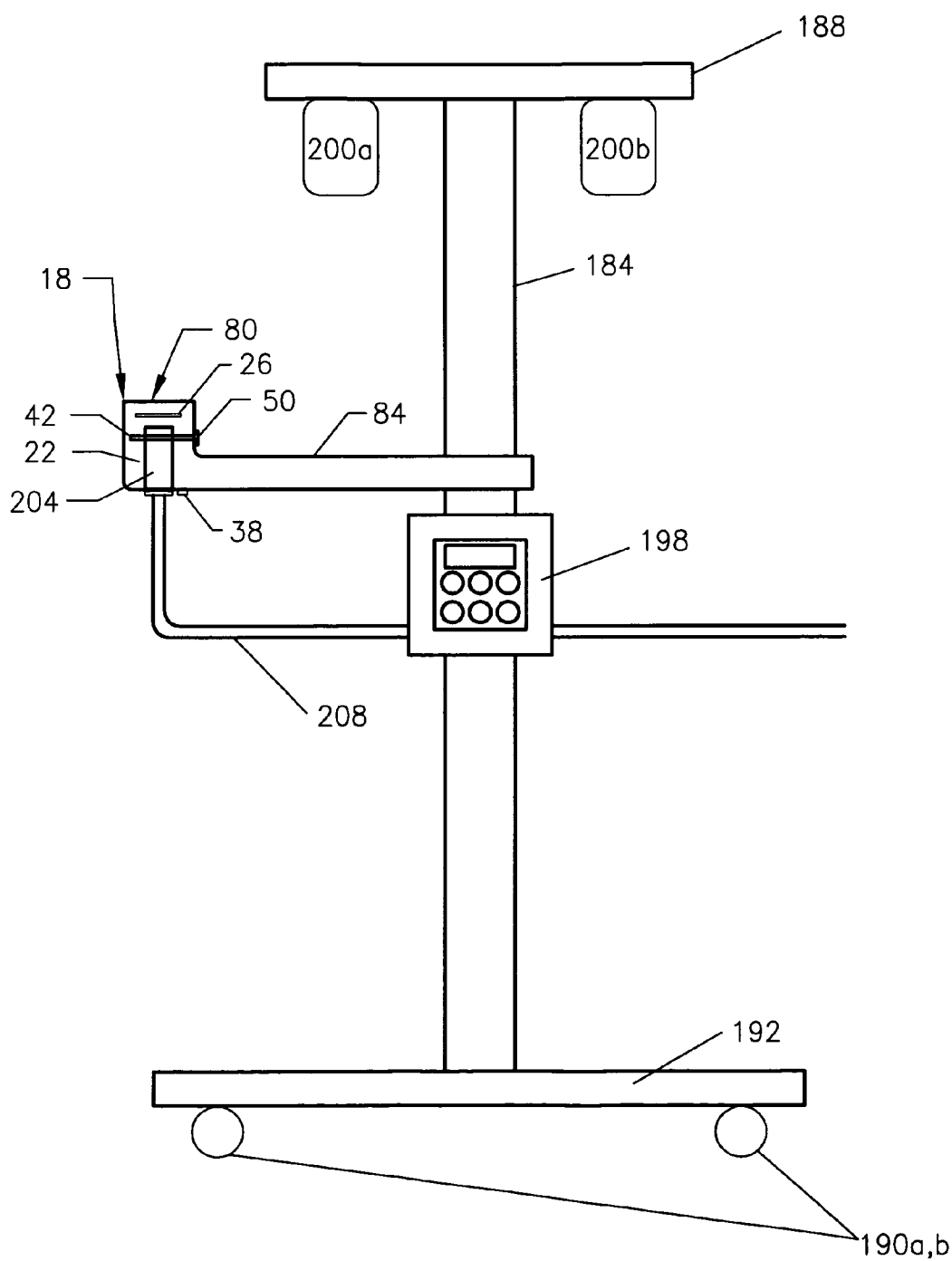
FIG. 12 illustrates a schematic of a fluid delivery system of the invention, including a fluid container having a discharge end, a fluid conduit, an IV stand, a fluid container holding device, and an infusion device.

FIG. 12 illustrates an embodiment of a fluid delivery system, generally designated 180, of the invention. The fluid delivery system 180 can include a fluid container 204 having a discharge end, a fluid conduit 208, an IV stand 184, a fluid container holding device 80, and an infusion device 198.

IV stands similar to the IV stand 184 illustrated herein are a common sight in most hospitals and medical facilities. The IV stand 184 has a base 192 with wheels 190*a,b* and a top 188 portion that supports hangers (not shown). Fluid bags 200*a,b* are the most common form of fluid container for infusion procedures, and are generally adapted to hang from the hangers disposed on the top portion 188 of IV stand 184. In this embodiment of the system, however, the IV bags 200*a,b* will not be used as the active fluid container. Rather, the bottle 204 will be the active fluid container.

One skilled in the art will recognize that the IV stand 184 is simply a preferred support structure and that this basic system would work just as effectively if the support structure were a desk, a table, a bed frame, a wall, a ceiling, a floor, a chair, a door, or any other support structure. Furthermore, the bottle 204 is also a preferred element of the embodiment, but could be effectively substituted for by any fluid container including, but not limited to, a carton, a jar, a can, a syringe, or a bag.

An infusion pump 198 is connected to IV stand 184, as is the fluid container holder 80. One skilled in the art will recognize that there are a plurality of different medical infusion devices, such as syringe pumps, that will be effective in the fluid delivery system disclosed herein.

The fluid container holder 80 comprises a base 18 defining an at least partially substantially concave region 22 adapted to engage or hold at least a portion of a fluid container. In this case, the active fluid container is a bottle 204 that has no flanges; therefore the substantially horizontal groove 26 is not used. The bottle 204 is engaged by or held against the base 18 by the forwardly extending gate 42, which is secured at a desired extended position by the second screw lock 50. The forwardly extending platform 34 (as best shown in FIGS. 2-7) has an at least partially substantially curved region 92 that is adapted to fit around at least a portion of the neck of bottle 204 to prevent the bottle 204 from sliding out from between the base 18 and the gate 42.

The discharge end of bottle 204 is operatively connected to IV tubing 208 that allows fluid to travel from the bottle 204 to the patient (not shown). The infusion pump 198 interacts with the tubing 208 to draw fluid from bottle 204 and deliver it to the patient.

Figure 13:
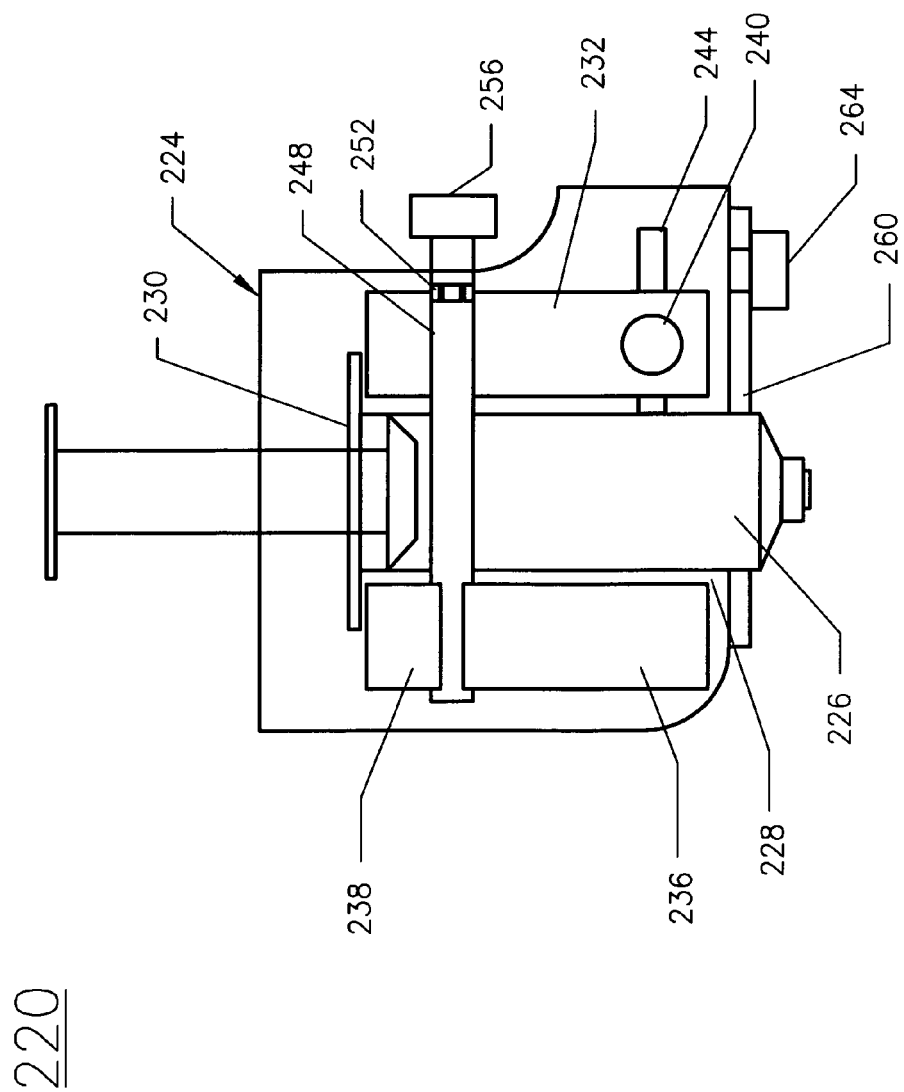
FIG. 13 illustrates a front plan schematic view of another embodiment of the fluid container holding device of the invention in which a fluid container is held.

FIG. 13 illustrates a front plan view of another embodiment of the fluid container holding device of the invention. This fluid container holding device, generally designated 220, comprises a base 224 that is adapted to engage or hold at least a portion of a fluid container, which is this embodiment can be a syringe 226.

The base 224 comprises a first protrusion 232, a second protrusion 236, and a third protrusion 238. The base 224 and protrusions of the base define a region 228 adapted to engage or hold at least a portion of the syringe 226. As shown in FIG. 13, the top of protrusions 232 and 238 may serve as a surface upon which the flange 230 of syringe 226 may rest when the syringe is retained as described in more detail below. The base 224 may also define a groove, such as groove 26 in the embodiment of FIGS. 1-10, with which to accommodate at least in part the flange 230 of syringe 226.

The first protrusion 232 is horizontally movable on the base 224, as it can be slid along the base 224 to come in to contact with at least a portion of syringe 226. The horizontal movement of protrusion 232 is facilitated by a channel 244 cut into the base 224. The first protrusion 232 can be locked into a desired position by a locking pin 240.

The second protrusion 236 and third protrusion 238 are stationary, and may be even manifested as a single protrusion. Whether manifested singly or separately, the second and third protrusion 236 and 238 define a space that is adapted to accept a gate 248, as best shown in FIG. 13. The gate 248 is horizontally rotatable around hinge 252. It is capable of rotating from an open position, in which the gate extends forward, to a closed position, in which the gate 248 rests between the second protrusion 236 and third protrusion 238. The gate 248 is shown in a closed position. In the closed position, the gate 248 is adapted to hold or engage at least a portion of the syringe 226 against the base 224. In addition, gate 248 is capable of being forwardly extended because it is connected to a support arm (not shown, but similar to support arm 94 shown in FIG. 2). The support arm can be secured in the desired position by a locking pin 256.

The fluid container is thus retained between the first protrusion 232 and the second and third protrusions 236 and 238 and against base 224 by a closure, which includes the gate 248 and its associated support arm. As with the embodiment of FIGS. 1-10, other types of closures would be effective in retaining the fluid container in position, for example, a strap, a rope, tape, or even a secondary base.

The syringe 226 can be further secured by a platform 260. The platform 260 is capable of being forwardly extended and can be locked into a desired position by another locking pin 264. In addition, the platform 260 defines a region adapted to hold or engage at least a portion of the fluid container. When this embodiment is used to secure a syringe 226, a portion of the platform 260 partially encircles the neck of syringe 226.

The presently preferred and alternative embodiments for carrying out the invention have been set forth in detail according to the Patent Act. Persons of ordinary skill in the art to which this invention pertains may nevertheless recognize alternative ways of practicing the invention without departing from the spirit of the following claims. Consequently, all changes and variations that fall within the literal meaning, and range of equivalency, of the claims are to be embraced within their scope. Persons of such skill will also recognize that the scope of the invention is indicated by the claims below rather than by any particular example or embodiment discussed or shown in the foregoing description.

What is claimed is:

1. An apparatus for holding a fluid container, said apparatus comprising:
    (a) a primary base defining a region adapted to engage at least a portion of the fluid container;
    (b) a platform operatively connected to said primary base and adapted to engage at least a portion of the fluid container; and
    (c) a closure operatively connected to said primary base for holding at least a portion of the fluid container against said primary base, wherein said closure includes:
    (d) a first support arm adjustably connected to said primary base;
    (e) a second support arm connected to said primary base; and
    (f) a gate operatively connected to said first support arm and therein enabled to be moved between a closed position in which said gate interlinks said first and said second support arms to enable the fluid container to be securely held against said primary base and an open position in which access and egress to said primary base is provided to the fluid container; wherein said closure further includes:
    (g) a channel defined within said first support arm; and
    (h) a screw lock for anchoring said first support arm into said primary base via said channel, with said first support arm and said gate therewith being enabled to be both extendible from and retractable towards said primary base via said channel when said screw lock is loosened.

2. The apparatus of claim 1; wherein said gate is connected to said first support arm via at least one hinge.

3. The apparatus of claim 1 wherein said closure is one of a strap, tape, and a secondary base adjustably interconnected with said primary base via at least one support arm.

4. The apparatus of claim 1 wherein said region is one of at least partially concave, at least partially convex, and at least partially substantially planar.

5. The apparatus of claim 1 wherein said region defines at least one groove for engaging at least a part of the fluid container.

6. The apparatus of claim 1 wherein the fluid container is one of a syringe and a bottle.

7. The apparatus of claim 1 wherein said platform is adjustably connected to said primary base approximate a bottom thereof and defines a region that is adapted to at least one of engage and at least partially hold said portion of the fluid container thereat.

8. The apparatus of claim 1 wherein said platform is adjustable to any point between and including a fully extended position and a fully retracted position, said apparatus further including a locking mechanism for releasably anchoring said platform into a position appropriate for the type of the fluid container said apparatus is being used to hold.

9. The apparatus of claim 1 wherein said platform is adapted to at least partially encircle at least a portion of a neck of the fluid container.

10. The apparatus of claim 1 further comprising a mounting arm connected to said primary base and adapted for removably mounting said apparatus to an external structure.

11. The apparatus of claim 10 wherein said primary base is adapted to at least one of tilt and rotate.

* * * * *